US00PP08811P

United States Patent [19]

Brooks

[11] Patent Number: Plant 8,811

[45] Date of Patent: Jun. 28, 1994

[54] ANTHURIUM PLANT BROOKS NO. 1

[75] Inventor: Harold K. Brooks, Patillas, P.R.

[73] Assignee: Oglesby Plant Laboratories Inc., Altha, Fla.

[21] Appl. No.: 110,461

[22] Filed: Aug. 23, 1993

[51] Int. Cl.[5] ..... A01H 5/00

[52] U.S. Cl. ..... Plt./88.1

[58] Field of Search ..... Plt. 88.1

*Primary Examiner*—James R. Feyrer

*Attorney, Agent, or Firm*—Henderson & Sturm

[57] ABSTRACT

A new variety of Anthurium is provided. The leaves are large, thick and dark green. The large double red spathes have a peculiar boat-like shape and are held by strong peduncles.

3 Drawing Sheets

SUMMARY OF THE INVENTION

This invention relates to a new and distinct Anthurium cultivar which is outstanding because of its large, thick, dark green leaves and large, double, red spathes of a peculiar boat-like shape held on strong peduncles, and primarily selected for those characteristics being so selected from a planning of Anthurium being grown near Altha, Fla. in a cultivated area.

ORIGIN AND ASEXUAL REPRODUCTION

Asexual reproduction of this cultivar by tissue culture was directed by me, such reproducting establishing that the plant does in fact maintain the characteristics described, in successive generations.

It should be noted that the plant was initially selected where grown in or near Altha, Fla. and has since been reproduced by plant tissue culture in the vicinity of Altha, Fla. with the characteristics stated, found to be maintained through successive generations as before recited.

The cultivar may further be described as having a number of distinctive characteristics which are enumerated in the succeeding specific description but broadly stated as comprising large, thick dark green leaves and large double red spathes of a peculiar boat-like shape held on strong peduncles, makes this cultivar suitable for commercial distribution as a flowering pot plant.

I have chosen to identify this new cultivar as Anthurium 'Brooks No. 1'.

It is possible that other identification will be adopted in the trade, but the name selected will serve for the purposes hereof.

BRIEF DESCRIPTION OF THE PHOTOGRAPHS

The accompanying photographs show as nearly true as it is reasonably possible to make the same, in a color illustration of this character, typical specimens of the plant parts of the new variety. The plants of the new variety were approximately 24 months from cutting propagation.

In the photographs:

FIG. 1 discloses the new variety;

DETAILED DESCRIPTION

Figure 1:
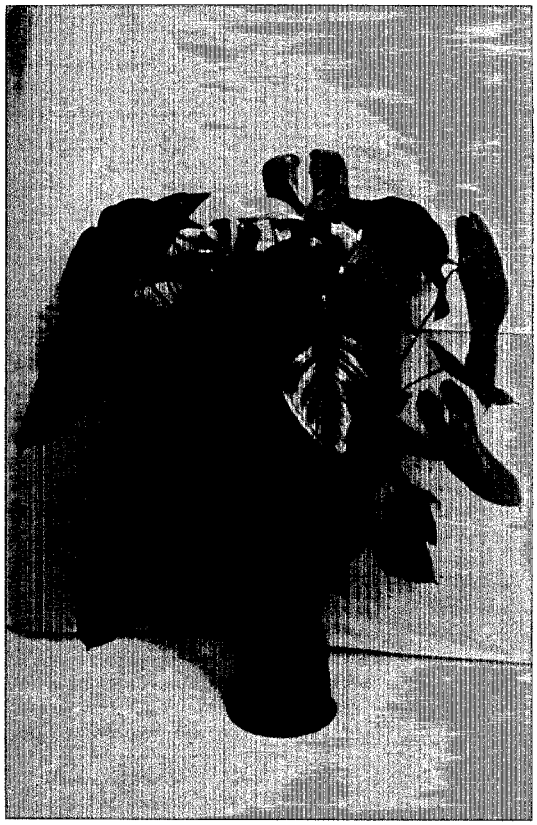
Figure 2:
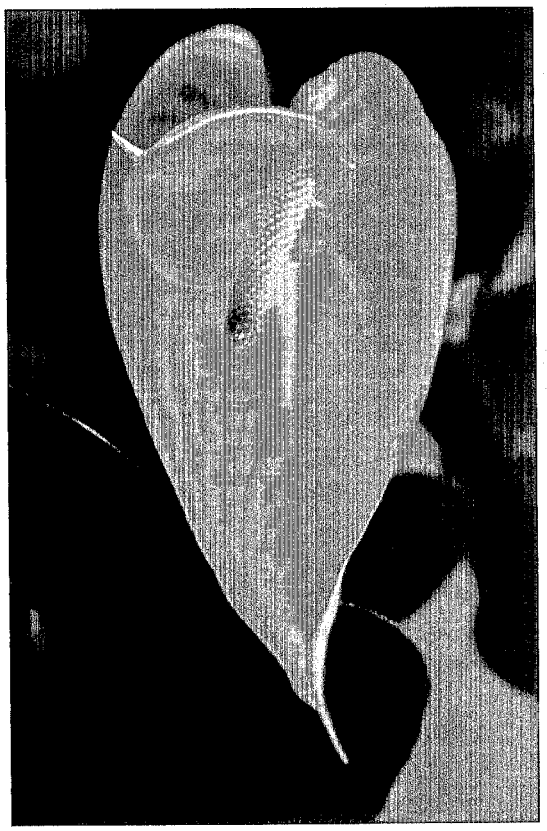
FIG. 2 illustrates the spathe and spadix of a mature flower.
Figure 4:
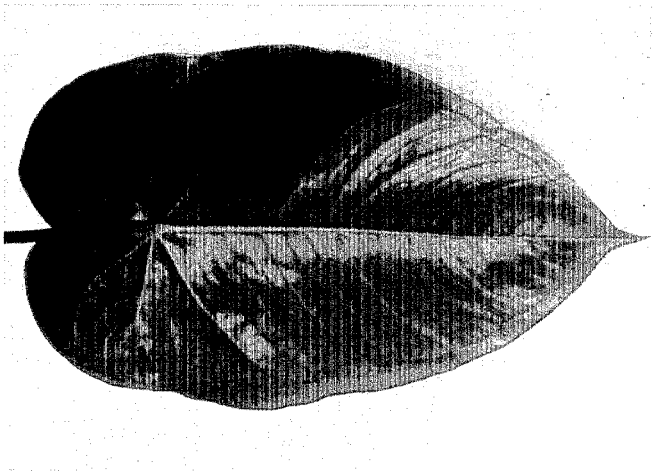
FIG. 4 illustrates the bottom of a mature leaf.
Figure 3:
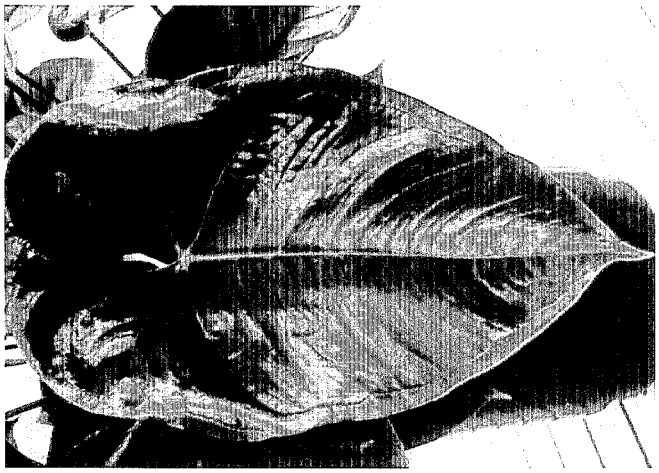
FIG. 3 illustrates a top of a mature leaf.

In order to more specifically identify the cultivar descriptive details are set forth hereinafter, along with related aspects of the plant which serve to distinguish the same all colors being noted as compared with The Royal Horticultural Society Colour Chart. The measurements and colors were recorded in December from mature plants grown in 10-inch diameter pots in the vicinity of Altha, Fla. The three newest, fully developed units of each organ type (except for the flower) from the main stem were measured from each plant. The two or three newest, fully opened flowers from each plant were measured.

Parentage:

*Seed parent.*—*Anthurium andreanum.*

*Pollen parent.*—*Anthurium Calypso type.*

Propagation: Plant Tissue Culture started near Altha, Fla.

Plant Description:

*Stem.*—Smooth, yellow-green (144 D, 145 B).

*Lenticels.*—Not obvious.

*Petioles.*—43–64 cm. Smooth. Young petioles, yellow-green (152 A-B). Mature petioles yellow-green (146 A), slightly lighter (146 B) near the top, with the lightest (146 C) about 2.5–3.5 cm adjacent to the leaf blade. They occasionally show some grayed-orange (176 A) coloration on the adaxial side.

*Leaves.*—Ovate, cuspidate tip. The leaf base shape depends on the stage of overall plant maturity when the leaf is formed. Leaves of young plants have cordate leaf bases. Leaves of mature plants have sagittate bases with a sinus typically extending to about ¼ of the leaf length. Edges of the sinus of a mature leaf curl outwards. Margins entire. At maturity, leaves range from 34–43 cm long by 20–26 cm wide.

*Color.*—Young expanding leaf yellow-green (similar to 146 A) adaxial and slightly lighter (146 B) abaxial. Polished. Mature leaf yellow-green (147 A) adaxial and yellow-green (146 A-B) abaxial. Slightly polished.

*Veins.*—Primary veins prominent on a mature leaf. They are particularly prominent and protrude from leaf surface near leaf blade attachment to the petiole from which they radiate towards the leaf margin. Exceptions to the above are sunken veins that serve the lobes. The primary veins that run more-or-less parallel to the margin are sunken. Veins on a mature leaf are yellow-green (146 B-C), lighter than the rest of the blade. Color of the young leaf's veins approximates the leaf surface color.

*Leaf sheath.*—12–17 cm long. Surrounds young leaf during early developmental stages and is directly attached to the stem below the leaf attachment. The leaf sheath surrounding the youngest immature leaf is yellow-green (144 C-D) at the base, especially toward the edges. This color is darker (144 A-B, 146 A) toward the center and the top of the sheath. A distinct yellow-green (144 A-B) rib protrudes from the sheath's surface in the center from the top almost to its base. There are variable amounts of grayed-red (182 A) coloration on both sides of the rib. With age sheath becomes more pale, but the yellow-green rib and ome of the grayed-red coloration remain.

Flower:

*Type.*—Spadix and two spathes. Spathes tightly rolled around spadix before opening. When outer spathe first opens, the inner spathe is still tightly rolled around spadix. When the flower is completely open, both spathes have a boat-like shape. Spathes are attached to the peduncle approximately 2–5 mm apart. The long axis of the inner spathe is oblique to that of the outer spathe. Each spathe is slightly puckered, ovate, has cordate base, cuspidate tip, and is slightly polished. The outer spathe is 6–9 cm wide, 13–19.5 cm long (width to length ratio 0.3:1 to 0.6:1) and 3–5.5 cm deep. The inner spathe is 4–6.5 cm wide by 6.5–8 cm long (width to length ratio 0.6:1 to 0.8:1).

*Spathe color.*—Both spathes are similar in color during most of their development. Newly opened flowers are red (53 C) adaxial and red (51 A-B, 53 D, 54 A-B) abaxial. The tips of both spathes are yellow-green (144 C, 145 A-B) on the abaxial side as are segments of veins (especially of the midrib) near the base of the outer spathe. Mature flowers are similar to young flowers except that as flowers age additional colors develop with yellow-green (146 A-B) the most common. In the outer spathe the yellow-green eventually predominates the basal abaxial area, and variable amounts of grayed-red (178 A-B) develop in abaxial side nearer the tip. The inner spathe develops similar coloration in the abaxial side, except that the grayed-red color may predominate. A mixture of yellow-green (146 A), grayed-red (178 A) and grayed-purple (183 A) also develops with age in the adaxial sides of both spathes, especially in the basal areas; predominating in that of the outer spathe but more limited in that of the inner spathe. Most of the ridges along the veins preserve red color in aging flowers.

*Spathe veines.*—Primary veins along ridges. Midrib of outer spathe even to slightly sunken except for basal end (approximately one-third length) which slightly protrudes from the surface.

*Peduncle.*—*46–64* cm long. Peduncle of the young flower is yellow-green (144 A), and slightly lighter near the spathe (146 C). Additionally, yellow-green (152 A-B) may also occur in variable amounts. Peduncles of mature flowers are yellow-green (146 A) in the lower half gradually merging in the upper half with progressively lighter shades, first (146 B) then (146 C) nearest the spathe. Some peduncles show some grayed-orange coloration (176 B), usually in the upper half.

Reproductive organs:

*Spadix.*—6–8 cm long, 9–15 mm wide at base. Three colors usually occur in the young spadix with the basal and largest zone red-purple (70 C-D), the central zone red (51 A-B), and the tip grayed-red (178 A-D). Three principal zones also occur in mature flowers where up to 5/6 of spadix below the tip contain gradations of purple with the lightest, red-purple (70 D), at the base and the darkest, purple (78 C), nearer the tip. A short red (51 A, 53 D, 54 A) zone follows immediately and grayed-red (178 A-B) is limited to approximately 5 mm at the tip. Spadix of old flower is a uniform grayed-purple (187 A).

*Stamens.*—Anthers and filaments not clearly visible.

*Flowering time.*—First 1–2 flowers appear after 7 months in a 6-inch diameter pot. From then on flowering is continuous. Full flowering is achieved within 12–14 months in a 10-inch diameter pot, where most of the flowers are held above leaves.

*Roots.*—Roots developed above soil line are fleshy and non-branching. Roots developed below the soil line branch poorly, but they have numerous root hairs.

*Diseases.*—No unusual susceptibility to diseases noted to date.

*Insects.*—No unusual susceptibility to insects noted to date.

*General observations.*—Anthurium *Brooks No. 1' is a robust cultivar. It has large, thick, dark green leaves. Large, double, red spathes of a peculiar boat-like shape, held on strong peduncles make it an attractive and unusual pot plant.*

The cultivar may be compared with known varieties along the following lines where observation were made on plants grown under similar conditions near Altha, Fla.

Anthurium 'Rosa' TM : 'Brooks No. 1' has larger thicker and darker green leaves, stronger peduncles, and darker red, double spathes.

Anthurium 'Miami Beauty' TM : 'Brooks No. 1' has larger and thicker leaves, stronger peduncles and lighter red, double spathes.

I claim:

1. A new and distinct cultivar of Anthurium, substantially as described and illustrated herein, characterized particularly as to novelty by its large, thick dark green leaves and large double red spathes of a peculiar boat-like shape held on strong peduncles providing a cultivar well suited as a flowering pot plant having no unusual susceptibility to the traditional Anthurium diseases and insects.

* * * * *